(12) United States Patent
Klemm et al.

(10) Patent No.: US 8,558,430 B2
(45) Date of Patent: Oct. 15, 2013

(54) RESONANT MOTOR UNIT AND ELECTRIC DEVICE WITH RESONANT MOTOR UNIT

(75) Inventors: Torsten Klemm, Eschborn (DE); Ingo Vetter, Karben (DE); Uwe Jungnickel, Koenigstein (DE); Benedikt Heil, Ober-Moerlen (DE); Kris Lueckel, Kronberg (DE)

(73) Assignee: Braun GmbH, Kronberg (DE)

( * ) Notice: Subject to any disclaimer, the term of this patent is extended or adjusted under 35 U.S.C. 154(b) by 153 days.

(21) Appl. No.: 13/213,865

(22) Filed: Aug. 19, 2011

(65) Prior Publication Data

US 2012/0066848 A1    Mar. 22, 2012

(30) Foreign Application Priority Data

Aug. 19, 2010  (EP) .................................. 10008644
Aug. 19, 2010  (EP) .................................. 10008645
Jul. 25, 2011  (EP) .................................. 11006064

(51) Int. Cl.
*H01L 41/08* (2006.01)

(52) U.S. Cl.
USPC ..................................... 310/317; 310/316.92

(58) Field of Classification Search
USPC ................ 310/317, 316.01, 316.02
See application file for complete search history.

(56) References Cited

U.S. PATENT DOCUMENTS

| | | |
|---|---|---|
| 2,798,241 A | 7/1957 | Cohen |
| 3,109,619 A | 11/1963 | Krug et al. |
| 3,220,039 A | 11/1965 | Dayton et al. |
| 3,417,417 A | 12/1968 | Rhodes |
| 3,461,874 A | 8/1969 | Martinez |
| 3,496,500 A | 2/1970 | Romary |
| 3,571,544 A | 3/1971 | Sheehan |
| 3,782,799 A | 1/1974 | Hansen |
| 3,796,850 A | 3/1974 | Moreland, II et al. |
| 3,802,420 A | 4/1974 | Moffat et al. |
| 3,810,147 A | 5/1974 | Lichtblau |
| 3,904,841 A | 9/1975 | Swatman |
| 4,156,620 A | 5/1979 | Clemens |
| 4,274,070 A | 6/1981 | Thiene |

(Continued)

FOREIGN PATENT DOCUMENTS

| | | | |
|---|---|---|---|
| AU | 2005100387 A4 | 5/2005 | |
| CH | 688 537 A5 | 11/1997 | |

(Continued)

OTHER PUBLICATIONS

U.S. Appl. No. 13/557,243, filed Jul. 25, 2012, Utsch et al.

(Continued)

*Primary Examiner* — Mark Budd
(74) *Attorney, Agent, or Firm* — John P. Colbert; George H. Leal

(57) ABSTRACT

A resonant motor unit that has a resonant motor, a control unit, a measurement unit, and an evaluation unit is described. The control unit drives the resonant motor at a driving frequency, short-circuits the resonant motor during at least a first short-circuiting phase in successive driving cycles and concludes the first short-circuiting phases by switching off the current flow through the resonant motor at least at a predetermined first time instant within the driving cycles. The measurement unit successively measures at least a first voltage signal provided by the resonant motor at the predetermined first time instant, and the evaluation unit for determines whether the first voltage signal has changed between successive measurements.

15 Claims, 4 Drawing Sheets

(56) References Cited

U.S. PATENT DOCUMENTS

| | | |
|---|---|---|
| 4,333,197 A | 6/1982 | Kuris |
| 4,349,814 A | 9/1982 | Akehurst |
| 4,352,098 A | 9/1982 | Stephen et al. |
| 4,365,376 A | 12/1982 | Oda et al. |
| 4,371,118 A | 2/1983 | Sontheimer et al. |
| 4,374,354 A | 2/1983 | Petrovic et al. |
| 4,413,199 A | 11/1983 | Fischer |
| 4,420,851 A | 12/1983 | Wiener |
| 4,492,574 A | 1/1985 | Warrin et al. |
| 4,502,497 A | 3/1985 | Siahou |
| 4,506,400 A | 3/1985 | Klein |
| 4,514,172 A | 4/1985 | Behringer |
| 4,523,083 A | 6/1985 | Hamilton |
| 4,546,266 A | 10/1985 | Zenick et al. |
| 4,595,849 A | 6/1986 | Cuenoud |
| 4,595,850 A | 6/1986 | Woog |
| 4,603,448 A | 8/1986 | Middleton et al. |
| 4,682,584 A | 7/1987 | Pose |
| 4,698,869 A | 10/1987 | Mierau et al. |
| 4,704,602 A | 11/1987 | Asbrink |
| 4,716,614 A | 1/1988 | Jones et al. |
| 4,736,207 A | 4/1988 | Siikaria et al. |
| 4,820,152 A | 4/1989 | Warrin et al. |
| 4,827,550 A | 5/1989 | Graham et al. |
| 4,845,796 A | 7/1989 | Mosley |
| 4,878,679 A | 11/1989 | Plank et al. |
| 4,900,252 A | 2/1990 | Liefke et al. |
| 4,910,634 A | 3/1990 | Pipkorn |
| 4,914,376 A | 4/1990 | Meyer |
| 5,014,794 A | 5/1991 | Hansson |
| 5,065,137 A | 11/1991 | Herman |
| 5,072,164 A | 12/1991 | Pruis et al. |
| 5,099,536 A | 3/1992 | Hirabayashi |
| 5,165,131 A | 11/1992 | Staar |
| 5,168,186 A | 12/1992 | Yashiro |
| 5,184,959 A | 2/1993 | Oryhon et al. |
| 5,189,751 A | 3/1993 | Giuliani |
| 5,217,478 A | 6/1993 | Rexroth |
| 5,233,323 A | 8/1993 | Burkett et al. |
| 5,259,083 A | 11/1993 | Stansbury, Jr. |
| 5,263,218 A | 11/1993 | Giuliani et al. |
| 5,269,794 A | 12/1993 | Rexroth |
| 5,274,735 A | 12/1993 | Okada |
| 5,289,604 A | 3/1994 | Kressner |
| 5,305,492 A | 4/1994 | Giuliani et al. |
| 5,309,590 A | 5/1994 | Giuliani et al. |
| 5,337,435 A | 8/1994 | Krasner et al. |
| 5,341,534 A | 8/1994 | Serbinski et al. |
| 5,355,544 A | 10/1994 | Dirksing |
| 5,367,599 A | 11/1994 | Okada |
| 5,378,153 A | 1/1995 | Giuliani et al. |
| 5,381,576 A | 1/1995 | Hwang |
| 5,392,028 A | 2/1995 | Pichl |
| 5,404,608 A | 4/1995 | Hommann |
| 5,448,792 A | 9/1995 | Wiedemann et al. |
| 5,476,384 A | 12/1995 | Giuliani et al. |
| 5,502,861 A | 4/1996 | Spieler et al. |
| 5,504,959 A | 4/1996 | Yukawa et al. |
| 5,524,312 A | 6/1996 | Tan et al. |
| 5,544,382 A | 8/1996 | Giuliani et al. |
| 5,561,881 A | 10/1996 | Klinger et al. |
| 5,576,693 A | 11/1996 | Tyren et al. |
| 5,577,285 A | 11/1996 | Drossler |
| 5,613,259 A | 3/1997 | Craft et al. |
| 5,617,503 A | 4/1997 | Fronen et al. |
| 5,617,601 A | 4/1997 | McDougall |
| 5,673,451 A | 10/1997 | Moore et al. |
| 5,693,042 A | 12/1997 | Boiarski et al. |
| 5,700,146 A | 12/1997 | Kucar |
| 5,732,432 A | 3/1998 | Hui |
| 5,749,885 A | 5/1998 | Sjostrom et al. |
| 5,760,580 A | 6/1998 | Tyren |
| 5,781,955 A | 7/1998 | Hendricks |
| 5,784,742 A | 7/1998 | Giuliani et al. |
| 5,799,356 A | 9/1998 | Kawashima |
| 5,812,065 A | 9/1998 | Schrott et al. |
| 5,815,872 A | 10/1998 | Meginniss, III et al. |
| 5,836,030 A | 11/1998 | Hazeu et al. |
| 5,864,288 A | 1/1999 | Hogan |
| 5,888,031 A | 3/1999 | Buck et al. |
| 5,897,315 A | 4/1999 | Nakayama et al. |
| 5,934,908 A | 8/1999 | Woog et al. |
| 5,939,983 A | 8/1999 | Rudell et al. |
| 5,943,723 A | 8/1999 | Hilfinger et al. |
| 5,955,799 A | 9/1999 | Amaya et al. |
| 5,974,615 A | 11/1999 | Schwarz-Hartmann et al. |
| 5,994,855 A | 11/1999 | Lundell et al. |
| 5,998,965 A | 12/1999 | Carlucci et al. |
| 6,017,354 A | 1/2000 | Culp et al. |
| 6,021,538 A | 2/2000 | Kressner et al. |
| 6,029,303 A | 2/2000 | Dewan |
| 6,043,646 A | 3/2000 | Jansseune |
| 6,098,288 A | 8/2000 | Miyagawa et al. |
| 6,133,701 A | 10/2000 | Gokturk et al. |
| 6,140,723 A | 10/2000 | Matsui et al. |
| 6,140,802 A | 10/2000 | Lundell et al. |
| 6,163,258 A | 12/2000 | Rudell et al. |
| 6,177,870 B1 | 1/2001 | Lian et al. |
| 6,193,510 B1 | 2/2001 | Tsimerman |
| 6,195,828 B1 | 3/2001 | Fritsch |
| 6,202,242 B1 | 3/2001 | Salmon et al. |
| 6,212,052 B1 | 4/2001 | Heuer et al. |
| 6,227,853 B1 | 5/2001 | Hansen et al. |
| 6,234,051 B1 | 5/2001 | Bareggi |
| 6,265,789 B1 | 7/2001 | Honda et al. |
| 6,322,573 B1 | 11/2001 | Murayama |
| 6,326,884 B1 | 12/2001 | Wohlrabe |
| 6,353,956 B1 | 3/2002 | Berge |
| 6,359,559 B1 | 3/2002 | Rudell et al. |
| 6,367,108 B1 | 4/2002 | Fritsch et al. |
| 6,389,633 B1 | 5/2002 | Rosen |
| 6,411,169 B1 * | 6/2002 | Yabe et al. ............ 331/116 FE |
| 6,422,566 B1 | 7/2002 | Rudell et al. |
| 6,441,571 B1 | 8/2002 | Ibuki et al. |
| 6,446,294 B1 | 9/2002 | Specht |
| 6,453,497 B1 | 9/2002 | Chiang et al. |
| 6,498,456 B2 | 12/2002 | Ettes et al. |
| 6,517,348 B1 | 2/2003 | Ram |
| 6,531,873 B1 | 3/2003 | Wohlrabe |
| 6,536,068 B1 | 3/2003 | Yang et al. |
| 6,538,402 B2 | 3/2003 | Gokturk et al. |
| 6,545,576 B1 | 4/2003 | Marchini et al. |
| 6,586,860 B1 * | 7/2003 | Iino et al. ................. 310/316.02 |
| 6,590,763 B2 | 7/2003 | Kishimoto |
| 6,611,780 B2 | 8/2003 | Lundell et al. |
| 6,623,698 B2 | 9/2003 | Keo |
| 6,636,135 B1 | 10/2003 | Vetter |
| 6,648,641 B1 | 11/2003 | Viltro et al. |
| 6,716,028 B2 | 4/2004 | Rahman et al. |
| 6,731,213 B1 | 5/2004 | Smith |
| 6,734,795 B2 | 5/2004 | Price |
| 6,735,802 B1 | 5/2004 | Lundell et al. |
| 6,750,747 B2 | 6/2004 | Mandell et al. |
| 6,754,928 B1 | 6/2004 | Rosen |
| 6,760,945 B2 | 7/2004 | Ferber et al. |
| 6,766,824 B2 | 7/2004 | Taylor |
| 6,792,640 B2 | 9/2004 | Lev |
| 6,798,169 B2 | 9/2004 | Stratmann et al. |
| 6,811,399 B2 | 11/2004 | Rahman et al. |
| 6,813,793 B2 | 11/2004 | Eliav |
| 6,845,537 B2 | 1/2005 | Wong |
| 6,850,167 B2 | 2/2005 | Rosen |
| 6,859,968 B2 | 3/2005 | Miller et al. |
| 6,868,919 B1 | 3/2005 | Manschitz et al. |
| 6,873,067 B2 | 3/2005 | Ichii et al. |
| 6,889,401 B2 | 5/2005 | Fattori et al. |
| 6,891,287 B2 | 5/2005 | Moret |
| 6,895,630 B2 | 5/2005 | Tini |
| 6,899,538 B2 | 5/2005 | Matoba |
| 6,918,300 B2 | 7/2005 | Grez et al. |
| 6,952,855 B2 | 10/2005 | Lev et al. |
| 6,954,961 B2 | 10/2005 | Ferber et al. |
| 6,958,553 B2 | 10/2005 | Ichii et al. |
| 6,964,076 B2 | 11/2005 | Zhuan |

(56) References Cited

U.S. PATENT DOCUMENTS

| | | | |
|---|---|---|---|
| 6,966,093 B2 | 11/2005 | Eliav et al. | |
| 6,973,694 B2 | 12/2005 | Schutz et al. | |
| 7,011,520 B2 | 3/2006 | Rahman et al. | |
| 7,024,717 B2 | 4/2006 | Hilscher et al. | |
| 7,067,945 B2 | 6/2006 | Grez et al. | |
| 7,086,111 B2 | 8/2006 | Hilscher et al. | |
| 7,117,555 B2 | 10/2006 | Fattori et al. | |
| 7,120,960 B2 | 10/2006 | Hilscher et al. | |
| 7,140,058 B2 | 11/2006 | Gatzemeyer et al. | |
| 7,174,972 B2 | 2/2007 | Kristen et al. | |
| 7,194,862 B2 | 3/2007 | Sattinger | |
| 7,207,080 B2 | 4/2007 | Hilscher et al. | |
| 7,248,892 B2 | 7/2007 | White et al. | |
| 7,258,546 B2 | 8/2007 | Beier et al. | |
| 7,258,747 B2 | 8/2007 | Vago et al. | |
| 7,288,863 B2 | 10/2007 | Kraus | |
| 7,307,397 B2 | 12/2007 | Izumi et al. | |
| 7,313,422 B2 | 12/2007 | White et al. | |
| 7,315,098 B2 | 1/2008 | Kunita et al. | |
| 7,334,283 B2 | 2/2008 | Kunita et al. | |
| 7,373,170 B2 | 5/2008 | White et al. | |
| 7,376,439 B2 | 5/2008 | White et al. | |
| 7,386,904 B2 | 6/2008 | Fattori | |
| 7,392,059 B2 | 6/2008 | White et al. | |
| 7,409,741 B2 | 8/2008 | Dworzan | |
| 7,411,511 B2 | 8/2008 | Kennish et al. | |
| 7,422,582 B2 | 9/2008 | Malackowski et al. | |
| 7,430,776 B2 | 10/2008 | Eliav | |
| 7,431,682 B2 | 10/2008 | Zeiler et al. | |
| 7,443,058 B2 | 10/2008 | Shimizu et al. | |
| 7,443,059 B2 | 10/2008 | Kobayashi et al. | |
| 7,448,108 B2 | 11/2008 | Gatzemeyer et al. | |
| 7,469,703 B2 | 12/2008 | France et al. | |
| 7,474,018 B2 | 1/2009 | Shimizu et al. | |
| 7,474,065 B2 | 1/2009 | Kraus | |
| 7,493,669 B2 | 2/2009 | Miller et al. | |
| 7,495,358 B2 | 2/2009 | Kobayashi et al. | |
| 7,520,016 B2 | 4/2009 | Kressner | |
| 7,521,840 B2 | 4/2009 | Heim | |
| 7,535,135 B2 | 5/2009 | Kardeis et al. | |
| 7,552,497 B2 | 6/2009 | Gatzemeyer et al. | |
| 7,562,121 B2 | 7/2009 | Berisford et al. | |
| 7,621,015 B2 | 11/2009 | Hilscher et al. | |
| 7,624,467 B2 | 12/2009 | Hilscher et al. | |
| 7,627,922 B2 | 12/2009 | Miller et al. | |
| 7,636,976 B2 | 12/2009 | Banning | |
| 7,646,117 B2 | 1/2010 | Shimizu et al. | |
| 7,654,271 B2 | 2/2010 | Wyatt et al. | |
| 7,661,172 B2 | 2/2010 | Hilscher et al. | |
| 7,673,360 B2 | 3/2010 | Hilscher et al. | |
| 7,676,875 B2 | 3/2010 | Cho | |
| 7,687,944 B2 | 3/2010 | Benning et al. | |
| 7,698,771 B2 | 4/2010 | Gall | |
| 7,712,174 B2 | 5/2010 | Shimizu et al. | |
| 7,732,978 B2 * | 6/2010 | Suzuki | 310/317 |
| 7,750,532 B2 | 7/2010 | Heim | |
| 7,770,251 B2 | 8/2010 | Hilscher et al. | |
| 7,774,886 B2 | 8/2010 | Hilscher et al. | |
| 7,784,136 B2 | 8/2010 | Gatzemeyer et al. | |
| 7,784,144 B2 | 8/2010 | Renault | |
| 7,810,199 B2 | 10/2010 | Kressner | |
| 7,827,644 B2 | 11/2010 | Eliav | |
| 7,845,039 B2 | 12/2010 | Chan et al. | |
| 7,849,549 B2 | 12/2010 | Hegemann et al. | |
| 7,861,348 B2 | 1/2011 | Chan | |
| 7,861,349 B2 | 1/2011 | Hilscher et al. | |
| 7,876,003 B2 | 1/2011 | Bax | |
| 7,877,832 B2 | 2/2011 | Reinbold | |
| 7,887,559 B2 | 2/2011 | Deng et al. | |
| 7,979,938 B2 | 7/2011 | Lilley et al. | |
| 7,979,939 B2 | 7/2011 | Hilscher et al. | |
| 8,015,648 B2 | 9/2011 | Hall | |
| 8,020,238 B2 | 9/2011 | Eliav et al. | |
| 8,021,065 B2 | 9/2011 | Lou | |
| 8,032,964 B2 | 10/2011 | Farrell et al. | |
| 8,032,965 B2 | 10/2011 | Asada et al. | |
| 8,035,487 B2 | 10/2011 | Malackowski | |
| 8,089,227 B2 | 1/2012 | Baertschi et al. | |
| 8,143,817 B2 | 3/2012 | Izumi et al. | |
| 8,181,301 B2 | 5/2012 | Hilscher et al. | |
| 8,185,991 B2 | 5/2012 | Kressner | |
| 8,218,711 B2 | 7/2012 | Neyer | |
| 8,264,105 B2 | 9/2012 | Bax | |
| 8,288,970 B2 | 10/2012 | Miller et al. | |
| 8,314,586 B2 | 11/2012 | Lumbantobing et al. | |
| 8,317,424 B2 | 11/2012 | Chenvainu et al. | |
| 8,336,155 B2 | 12/2012 | Crossman et al. | |
| 8,341,791 B2 | 1/2013 | Iwahori | |
| 2002/0003384 A1 * | 1/2002 | Iino et al. | 310/316.02 |
| 2002/0084707 A1 | 7/2002 | Tang | |
| 2002/0088068 A1 | 7/2002 | Levy et al. | |
| 2002/0127512 A1 | 9/2002 | Chen et al. | |
| 2002/0196113 A1 | 12/2002 | Rudd et al. | |
| 2003/0017874 A1 | 1/2003 | Jianfei et al. | |
| 2003/0097723 A1 | 5/2003 | Li | |
| 2003/0115694 A1 | 6/2003 | Pace | |
| 2004/0060137 A1 | 4/2004 | Eliav | |
| 2004/0068811 A1 | 4/2004 | Fulop et al. | |
| 2004/0119448 A1 * | 6/2004 | Wiegand et al. | 323/223 |
| 2004/0123409 A1 | 7/2004 | Dickie | |
| 2004/0128778 A1 | 7/2004 | Wong | |
| 2004/0191724 A1 | 9/2004 | Rahman et al. | |
| 2004/0255409 A1 | 12/2004 | Hilscher et al. | |
| 2005/0011022 A1 | 1/2005 | Kwong | |
| 2005/0011023 A1 | 1/2005 | Chan | |
| 2005/0037316 A1 | 2/2005 | Sholder | |
| 2005/0102776 A1 | 5/2005 | Mathur | |
| 2005/0128051 A1 | 6/2005 | Dickinson et al. | |
| 2005/0235438 A1 | 10/2005 | Motohashi et al. | |
| 2005/0271531 A1 | 12/2005 | Brown, Jr. et al. | |
| 2005/0272001 A1 | 12/2005 | Blain et al. | |
| 2005/0278877 A1 | 12/2005 | Akridge et al. | |
| 2006/0006764 A1 * | 1/2006 | Ganor et al. | 310/328 |
| 2006/0027246 A1 | 2/2006 | Wilkinson | |
| 2006/0032006 A1 | 2/2006 | Brown et al. | |
| 2006/0048315 A1 | 3/2006 | Chan et al. | |
| 2006/0048797 A1 | 3/2006 | Jung et al. | |
| 2006/0145871 A1 | 7/2006 | Donati et al. | |
| 2007/0000079 A1 | 1/2007 | Mori et al. | |
| 2007/0130705 A1 | 6/2007 | Chan et al. | |
| 2007/0234493 A1 | 10/2007 | Hilscher et al. | |
| 2008/0020351 A1 | 1/2008 | Hilscher et al. | |
| 2008/0022470 A1 | 1/2008 | Hilscher et al. | |
| 2008/0022501 A1 | 1/2008 | Hilscher et al. | |
| 2008/0022503 A1 | 1/2008 | Hilscher et al. | |
| 2008/0028549 A1 | 2/2008 | Hilscher et al. | |
| 2008/0032265 A1 | 2/2008 | Hilscher et al. | |
| 2008/0034515 A1 | 2/2008 | Hilscher et al. | |
| 2008/0083075 A1 | 4/2008 | Dickie | |
| 2008/0102419 A1 | 5/2008 | Sauter et al. | |
| 2008/0196735 A1 | 8/2008 | Wyatt et al. | |
| 2008/0254407 A1 | 10/2008 | Benning et al. | |
| 2008/0293009 A1 | 11/2008 | Winston | |
| 2009/0045696 A1 * | 2/2009 | Suzuki | 310/317 |
| 2009/0177125 A1 | 7/2009 | Pilcher et al. | |
| 2009/0183324 A1 | 7/2009 | Fischer et al. | |
| 2009/0211043 A1 | 8/2009 | Kressner | |
| 2009/0241276 A1 | 10/2009 | Hall et al. | |
| 2009/0243520 A1 | 10/2009 | Kashiwabara et al. | |
| 2009/0320221 A1 | 12/2009 | Masuko | |
| 2010/0132139 A1 | 6/2010 | Jungnickel | |
| 2010/0301783 A1 | 12/2010 | Luckel et al. | |
| 2010/0306934 A1 | 12/2010 | Headstrom | |
| 2011/0005015 A1 | 1/2011 | Iwahori et al. | |
| 2011/0041268 A1 | 2/2011 | Iwahori et al. | |
| 2011/0080122 A1 | 4/2011 | Klemm et al. | |
| 2011/0095711 A1 * | 4/2011 | Hsieh et al. | 318/116 |
| 2011/0107531 A1 | 5/2011 | Ye | |
| 2011/0138551 A1 | 6/2011 | Stopler et al. | |
| 2011/0181208 A1 | 7/2011 | Murata | |
| 2011/0181209 A1 | 7/2011 | Murata | |
| 2011/0181211 A1 | 7/2011 | Murata | |
| 2011/0203061 A1 | 8/2011 | Takahashi et al. | |
| 2011/0248085 A1 | 10/2011 | Hilscher et al. | |

(56) References Cited

U.S. PATENT DOCUMENTS

| | | |
|---|---|---|
| 2011/0252584 A1 | 10/2011 | Jousma et al. |
| 2011/0258793 A1 | 10/2011 | Jousma et al. |
| 2011/0273153 A1 | 11/2011 | Lepper et al. |
| 2012/0036665 A1 | 2/2012 | Cho |
| 2012/0042742 A1 | 2/2012 | Utsch et al. |
| 2012/0066848 A1 | 3/2012 | Klemm et al. |
| 2012/0151698 A1 | 6/2012 | Schaefer et al. |
| 2012/0198635 A1 | 8/2012 | Hilscher et al. |
| 2013/0025079 A1 | 1/2013 | Jungnickel et al. |
| 2013/0029289 A1 | 1/2013 | Utsch et al. |

FOREIGN PATENT DOCUMENTS

| | | |
|---|---|---|
| CN | 2048697 | 12/1989 |
| CN | 2124686 | 12/1992 |
| CN | 2149877 | 12/1993 |
| CN | 1098888 A | 2/1995 |
| CN | 2332378 | 8/1999 |
| CN | 1520788 A | 1/2004 |
| CN | 1778278 A | 11/2004 |
| CN | 1778279 A | 11/2004 |
| CN | 1843305 A | 4/2005 |
| CN | 1846651 A | 4/2005 |
| CN | 183043 A | 9/2006 |
| CN | 200980058 | 11/2007 |
| CN | 201055092 Y | 5/2008 |
| CN | 201403746 Y | 10/2008 |
| CN | 201295301 Y | 12/2008 |
| CN | 201187899 Y | 1/2009 |
| CN | 101427944 A | 5/2009 |
| CN | 201341578 Y | 11/2009 |
| CN | 20151881 U | 7/2010 |
| DE | 2413524 | 10/1975 |
| DE | 2826008 C2 | 6/1983 |
| DE | 3708801 A1 | 9/1988 |
| DE | 4036373 C2 | 11/1990 |
| DE | 3936714 | 5/1991 |
| DE | 3937852 | 5/1991 |
| DE | 4012413 | 10/1991 |
| DE | 4036479 | 5/1992 |
| DE | 42 01 027 A1 | 7/1992 |
| DE | 3880015 | 9/1993 |
| DE | 4422086 C1 | 6/1994 |
| DE | 4305013 | 8/1994 |
| DE | 19506129 | 2/1995 |
| DE | 19518935 | 5/1995 |
| DE | 94 11 158 U1 | 8/1995 |
| DE | 29608164 | 5/1996 |
| DE | 19627752 A1 | 7/1996 |
| DE | 19628574 | 3/1997 |
| DE | 19545324 | 6/1997 |
| DE | 1196 03 851 A1 | 8/1997 |
| DE | 29608167 | 9/1997 |
| DE | 29709865 U1 | 10/1997 |
| DE | 198 03 311 A1 | 8/1999 |
| DE | 29915858 U1 | 9/1999 |
| DE | 198 40 684 A1 | 3/2000 |
| DE | 19832607 | 5/2000 |
| DE | 199 13 945 A1 | 9/2000 |
| DE | 19921677 | 11/2000 |
| DE | 19923104 A1 | 11/2000 |
| DE | 10001502 | 3/2001 |
| DE | 10026513 | 5/2001 |
| DE | 201 12 320 U1 | 10/2001 |
| DE | 19953651 | 10/2001 |
| DE | 10135257 | 2/2002 |
| DE | 10045353 | 3/2002 |
| DE | 10045067 | 4/2002 |
| DE | 10101163 | 7/2002 |
| DE | 4243219 A1 | 12/2002 |
| DE | 10153863 | 5/2003 |
| DE | 10154946 | 5/2003 |
| DE | 102 47 698 | 4/2004 |
| DE | 10 2004 029 684 A1 | 12/2005 |
| DE | 10 2005 045 800 A1 | 4/2007 |
| DE | 197 27 018 B4 | 4/2007 |
| EP | 024992 | 6/1984 |
| EP | 046169 | 8/1984 |
| EP | 0085795 | 3/1987 |
| EP | 285915 | 12/1988 |
| EP | 0300345 | 1/1989 |
| EP | 0435329 | 7/1991 |
| EP | 440051 | 8/1991 |
| EP | 391967 B1 | 8/1992 |
| EP | 294548 B1 | 4/1993 |
| EP | 624079 | 10/1993 |
| EP | 634151 | 3/1994 |
| EP | 787469 A1 | 8/1997 |
| EP | 848921 | 6/1998 |
| EP | 1 231 706 A2 | 8/2002 |
| EP | 1267664 | 6/2004 |
| EP | 1379149 | 8/2004 |
| EP | 1244373 | 7/2006 |
| EP | 1 696 539 A1 | 8/2006 |
| EP | 1 737 110 A1 | 12/2006 |
| EP | 1 733 700 B1 | 8/2010 |
| EP | 2 262 083 A1 | 12/2010 |
| FR | 2832298 | 5/2003 |
| GB | 1167444 | 10/1969 |
| GB | 1246564 | 9/1974 |
| GB | 2082713 | 3/1982 |
| GB | 2117230 | 10/1983 |
| GB | 2146893 | 5/1985 |
| GB | 2376758 | 12/2002 |
| GB | 2 412 014 A | 9/2005 |
| JP | 1989083268 | 3/1989 |
| JP | 04-087127 | 3/1992 |
| JP | 04-269906 | 9/1992 |
| JP | 05-269024 | 10/1993 |
| JP | 06-01413 | 1/1994 |
| JP | 07-123600 | 5/1995 |
| JP | 07-177932 | 7/1995 |
| JP | 07-194862 | 8/1995 |
| JP | 08-000358 | 1/1996 |
| JP | 08-066325 | 3/1996 |
| JP | 08-117030 | 5/1996 |
| JP | 1996187125 | 7/1996 |
| JP | 08-275961 | 10/1996 |
| JP | 09-252843 | 9/1997 |
| JP | 1998005041 | 1/1998 |
| JP | 10-127346 | 5/1998 |
| JP | 10-243688 | 9/1998 |
| JP | 28-62873 | 3/1999 |
| JP | 199113638 | 4/1999 |
| JP | 11-318951 | 11/1999 |
| JP | 2000-253639 A | 9/2000 |
| JP | 2001-37788 | 2/2001 |
| JP | 2001-197676 | 7/2001 |
| JP | 2001/346816 | 12/2001 |
| JP | 2001-346816 | 12/2001 |
| JP | 2002/045379 | 2/2002 |
| JP | 2002/306867 | 10/2002 |
| JP | 2002/320399 | 10/2002 |
| JP | 2003/250233 | 9/2003 |
| JP | 2003/348888 | 12/2003 |
| JP | 2004/007890 | 1/2004 |
| JP | 2006-280830 | 10/2006 |
| JP | 2007-000693 | 1/2007 |
| JP | 1998137040 | 5/2008 |
| JP | 2009-100523 | 5/2009 |
| JP | 2010-035315 | 2/2010 |
| JP | 2010-125263 | 6/2010 |
| KR | 2003-0091408 | 12/2003 |
| KR | 10-2005-0043071 | 5/2005 |
| KR | 10-2007-0034649 | 3/2007 |
| KR | 10-0752601 | 8/2007 |
| KR | 10-2007-0107198 | 11/2007 |
| KR | 20-2008-0004243 | 10/2008 |
| KR | 10-2009-106306 | 10/2009 |
| NL | C 1030139 | 10/2005 |
| RU | 2 077 349 C1 | 7/1993 |
| RU | 2 129 826 C1 | 5/1999 |
| SE | 531 401 C2 | 3/2009 |

(56) References Cited

FOREIGN PATENT DOCUMENTS

| | | |
|---|---|---|
| SU | 749380 | 7/1980 |
| SU | 1542539 | 2/1990 |
| WO | WO 91/06258 | 5/1991 |
| WO | WO 95/33419 | 12/1995 |
| WO | WO 97/24079 | 10/1997 |
| WO | WO 98/24527 | 6/1998 |
| WO | WO-98/36703 A1 | 8/1998 |
| WO | WO 98/55274 | 10/1998 |
| WO | WO 99/20202 | 4/1999 |
| WO | WO 99/53562 | 10/1999 |
| WO | WO 00/39768 | 7/2000 |
| WO | WO 00/42584 | 7/2000 |
| WO | WO 00/47128 | 8/2000 |
| WO | WO 00/74591 | 12/2000 |
| WO | WO 01/08591 | 2/2001 |
| WO | WO 01/32052 | 5/2001 |
| WO | WO 01/47392 | 7/2001 |
| WO | WO 01/91603 | 12/2001 |
| WO | WO 02/093881 | 1/2002 |
| WO | WO 02/071972 A1 | 9/2002 |
| WO | WO 02/083257 | 10/2002 |
| WO | WO 02/098315 | 12/2002 |
| WO | WO 03/054771 | 7/2003 |
| WO | WO 2005/096882 A1 | 10/2005 |
| WO | WO 2008/015616 A2 | 2/2008 |
| WO | WO 2008/019864 A2 | 2/2008 |
| WO | WO 2008/098107 A2 | 8/2008 |
| WO | WO 2010/106522 A1 | 9/2010 |
| WO | WO 2010/106850 A1 | 9/2010 |
| WO | WO 2010/143156 A1 | 12/2010 |
| WO | WO 2011/044858 A1 | 4/2011 |
| WO | WO 2011/077289 A1 | 6/2011 |
| WO | WO 2011/077290 A1 | 6/2011 |

OTHER PUBLICATIONS

U.S. Appl. No. 13/557,240, filed Jul. 25, 2012, Utsch et al.
U.S. Appl. No. 13/190,284, filed Jul. 25, 2011, Utsch et al.
U.S. Appl. No. 13/557,245, filed Jul. 25, 2011, Jungnickel et al.
U.S. Appl. No. 13/190,293, filed Jul. 25, 2011, Ziegler et al.
U.S. Appl. No. 13/450,657, filed Apr. 19, 2012, Hilscher et al.
U.S. Appl. No. 13/166,894, filed Jun. 23, 2011, Hilscher et al.
U.S. Appl. No. 12/627,367, filed Nov. 30, 2009, Hilscher et al.
U.S. Appl. No. 11/888,152, filed Jul. 31, 2007, Hilscher et al.
Office Action from U.S. Appl. No. 10/872,075, dated Mar. 24, 2006.
Office Action from U.S. Appl. No. 10/872,075, dated May 15, 2007.
Office Action from U.S. Appl. No. 10/872,075, dated Jun. 4, 2009.
Office Action from U.S. Appl. No. 10/872,075, dated Aug. 1, 2006.
Office Action from U.S. Appl. No. 10/872,075, dated Oct. 31, 2007.
Office Action from U.S. Appl. No. 10/872,075, dated Dec. 10, 2008.
Office Action from U.S. Appl. No. 10/872,075, dated Dec. 27, 2006.
Office Action from U.S. Appl. No. 11/888,386, dated Dec. 3, 2009.
Office Action from U.S. Appl. No. 09/811,080, dated Feb. 3, 2004.
Office Action from U.S. Appl. No. 09/811,080, dated Oct. 1, 2004.
Office Action from U.S. Appl. No. 10/241,274, dated Jan. 14, 2005.
Office Action from U.S. Appl. No. 10/241,274, dated Sep. 1, 2006.
Office Action from U.S. Appl. No. 10/662,237, dated Feb. 18, 2005.
Office Action from U.S. Appl. No. 10/871,469, dated Jan. 9, 2007.
Office Action from U.S. Appl. No. 10/871,469, dated Jul. 25, 2006.
Office Action from U.S. Appl. No. 10/871,469, dated Aug. 24, 2005.
Office Action from U.S. Appl. No. 10/871,469, dated Dec. 27, 2007.
Office Action from U.S. Appl. No. 10/872,016, dated Feb. 7, 2006.
Office Action from U.S. Appl. No. 10/872,016, dated Feb. 23, 2007.
Office Action from U.S. Appl. No. 10/872,016, dated Mar. 7, 2008.
Office Action from U.S. Appl. No. 10/872,016, dated Apr. 10, 2009.
Office Action from U.S. Appl. No. 10/872,016, dated Jun. 24, 2005.
Office Action from U.S. Appl. No. 10/872,016, dated Jul. 10, 2006.
Office Action from U.S. Appl. No. 10/872,016, dated Sep. 20, 2006.
Office Action from U.S. Appl. No. 10/872,016, dated Nov. 9, 2009.
Office Action from U.S. Appl. No. 11/257,603, dated Jan. 18, 2007.
Office Action from U.S. Appl. No. 11/257,603, dated Mar. 21, 2008.
Office Action from U.S. Appl. No. 11/257,603, dated May 15, 2007.
Office Action from U.S. Appl. No. 11/257,603, dated Aug. 30, 2007.
Office Action from U.S. Appl. No. 11/257,603, dated Sep. 20, 2006.
Office Action from U.S. Appl. No. 11/257,603, dated Nov. 25, 2008.
Office Action from U.S. Appl. No. 11/763,338, dated Mar. 24, 2009.
Office Action from U.S. Appl. No. 11/763,338, dated Jul. 10, 2008.
Office Action from U.S. Appl. No. 11/763,338, dated Dec. 4, 2008.
Office Action from U.S. Appl. No. 11/888,212, dated Mar. 17, 2009.
Office Action from U.S. Appl. No. 11/888,212, dated Mar. 21, 2008.
Office Action from U.S. Appl. No. 11/888,250, dated Jun. 30, 2008.
Office Action from U.S. Appl. No. 11/888,251, dated Mar. 17, 2009.
Office Action from U.S. Appl. No. 11/888,251, dated Mar. 21, 2008.
Office Action from U.S. Appl. No. 11/888,386, dated Mar. 3, 2009.
Office Action from U.S. Appl. No. 11/890,083, dated Mar. 16, 2009.
PCT Search Report for PCT/EP 01/02844, dated Aug. 8, 2001.
PCT Search Report for PCT/EP 01/02862, dated Jul. 31, 2001.
PCT Search Report for PCT/EP 02/01724, dated Jul. 17, 2002 for U.S. Appl. No. 10/241,274.
Finkenzeller, Laus, "RFID-Handbuch, Grundlagen und praktische Anwendungen induktiver Funkanlagen, Transponder und kontaktloser Chipkarten" [Trans: "RFID Handbook. Fundamentals and Practical Applications to Inductive Radio Communications, Transponders and Contactless Chip Cards"], Carl Hanser Verlag Munchen, $2^{nd}$ Edtiion, Chapter 3, pp. 29-58 w/title page and Impressum. Contents pp. vii-xviii, and Appendices 15.2 "Standards" and 15.3 "Literature" on pp. 393-406.
Herzer, Gieselher, "Der grosse Lauschangriff auf Ladendiebe" [trans1. "The great surveillance of shoplifters"] in Physikalische Blaetter [trans1: Physics Letters] vol. 57, (2001), No. 5, pp. 43-48.
Package rear and bottom panels of Bausch & Lomb Interplak Model PB-4B, marked © 1990 (color, 1 sheet).
Color photographs of Bausch & Lomb "Interplak" Model PB-6 style Handpiece with waterproof electronic travel protection switch (believed circa 1992 on sale in the United States) (6 views).
Package rear and bottom panels of Bausch & Lomb Interplak Model PB-6, marked © 1992 (color, 1 sheet).
Product use instructions to Bausch & Lomb Interplak travel-style "Voyager" model TK-2 marked © 1991 (6 photocopies sheets containing cover and pp. 1-10).
"RFID Made Easy" Handbook by EM Microelectronic-Marin SA, 2074 Marin, Switzerland, copr 2000 and dated Mar. 2001,, Rev. C/350, pp. 1-33.
Use instructions to Braun D5 electric toothbrush Type 4726 on sale in US, circa 1991, including description of "Travel lock" switch.
Color photographs of Bausch & Lomb "Interplak" Model PB-4B style Handpiece with travel protection switch and Toothbrush attachment (handpiece stamped "1D IA", believed circa 1992 on sale in the United States) (2 sheets with 7 views).
PCT International Search Report dated Nov. 2, 2011.
European Search Report for EP 11 00 6065 dated Feb. 27, 2012.
Pct Search Report for PCT/IB2012/053780 dated Jun. 21, 2012.
PCT International search Report dated Oct. 28, 2011.
PCT International Search Report for PCT/IB2011/053665 dated Nov. 23, 2012.
PCT International Search Report for PCT/IB2012/053804—dated Nov. 29, 2012.

* cited by examiner

RESONANT MOTOR UNIT AND ELECTRIC DEVICE WITH RESONANT MOTOR UNIT

FIELD OF THE INVENTION

The present invention is generally related to resonant motor units and electric devices comprising a resonant motor unit, as well as methods of controlling a resonant motor.

BACKGROUND OF THE INVENTION

A resonant motor may be controlled based on the load of the resonance motor. In order to accomplish such a control, the motor current or the peak amplitude of the moving motor armature of the resonant motor may be measured. This allows for the resonant motor to be controlled such that constant peak amplitude is always achieved independent of the load of the motor. Such a control is relatively complex and requires further elements in the control loop such as a position detector measuring the peak amplitude. In a situation where only a simple control is required, these solutions are relatively costly.

It is thus a desire to provide a resonant motor unit and a method of controlling a resonant motor in a relatively simple way.

SUMMARY OF THE INVENTION

In accordance with at least some embodiments, there is provided a resonant motor unit having a resonant motor, a control unit for driving the resonant motor at a driving frequency, for short-circuiting the resonant motor during at least a first short-circuiting phase in successive driving cycles and for concluding the first short-circuiting phases by switching off the current flow through the resonant motor at least at a predetermined first time instant within the driving cycles, a measurement unit for successively measuring at least a first voltage signal provided by the resonant motor at the predetermined first time instant, and an evaluation unit for determining whether the first voltage signal has changed between successive measurements.

In accordance with at least some embodiments, there is provided a method of controlling a resonant motor having the acts of driving the resonant motor at a driving frequency, short-circuiting the resonant motor during at least a first short-circuiting phase, switching off a current flow through the resonant motor at least at a predetermined first time instant, measuring at least a first voltage signal provided by the resonant motor at the predetermined first time instant, and evaluating whether the first voltage signal has changed between successive measurements.

BRIEF DESCRIPTION OF THE DRAWINGS

The present disclosure is further elucidated by detailed description of general embodiments of resonant motor units or control methods of resonant motors and by a detailed description of example embodiments, where reference is made to figures. In the figures

DETAILED DESCRIPTION OF THE INVENTION

A resonant spring-mass system, such as a resonant motor (which may also be called an oscillating motor or a vibrating motor) has a resonance frequency $f_R(m;k)$ that is dependent on the relevant mass m and the relevant spring constant $k_s$. The resonant spring-mass system can be excited by a periodic driving force F(t) having a driving frequency $f_d$, which results in a driven periodic (typically sinusoidal) movement of the mass.

In some embodiments, a resonant motor has a stator comprising a motor coil (which may be secured to a housing of an electric device in which the resonant motor is disposed) and a movably mounted motor armature comprising one or several permanent magnets. In an unpowered state, the movably mounted motor armature is held in a rest position by a return force that in an embodiment may be provided by a spring or a spring arrangement. When an alternating supply voltage is provided at the motor coil (i.e. energy is introduced into the resonant motor), the developing electromagnetic field of the motor coil drives the movably mounted motor armature into a periodic movement. At least some of the movement of the motor armature is against the return force provided by the return force element. As long as energy is continuously provided to replace the energy consumed by the resonant motor, the resonant motor may achieve and then stay in an equilibrium state in which the peak amplitude of the moving motor armature is kept constant as long as the load of the resonant motor is kept constant.

The frequency $f_m$ of the driven periodic movement of the motor armature is determined by the driving frequency $f_d$, i.e. $f_m=f_d$. The periodic driving force and the driven periodic movement have a defined phase shift $\phi$ that depends, inter alia, on the difference between the driving frequency $f_d$ and the effective resonance frequency $f_r$. When the resonant motor (or in general: a resonant spring-mass system) is driven at its effective resonance frequency, i.e. $f_d=f_r$, the driven periodic movement has a phase shift of $\phi=-\pi/2$, i.e. $\phi=-90$ degrees, to the periodic driving force. The spring-mass system is driven with highest efficiency when the driving frequency and the resonance frequency coincide.

Figure 1:
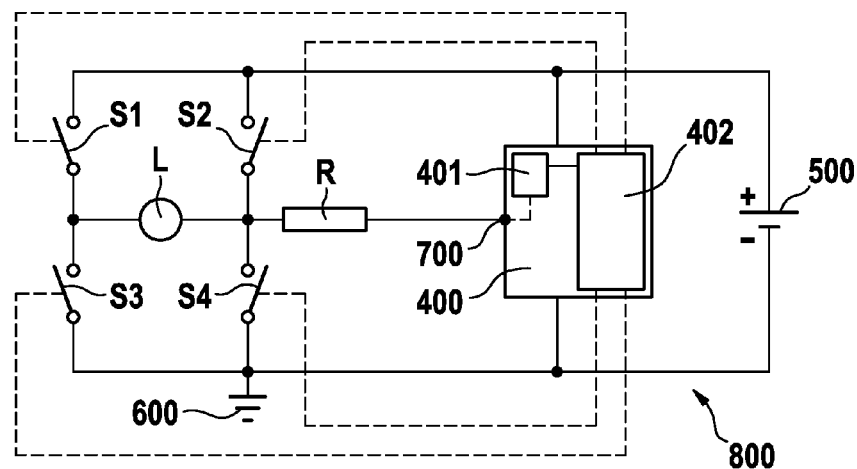
FIG. 1 is a depiction of a resonant motor unit having a resonant motor and a control circuitry.
Figure 6:
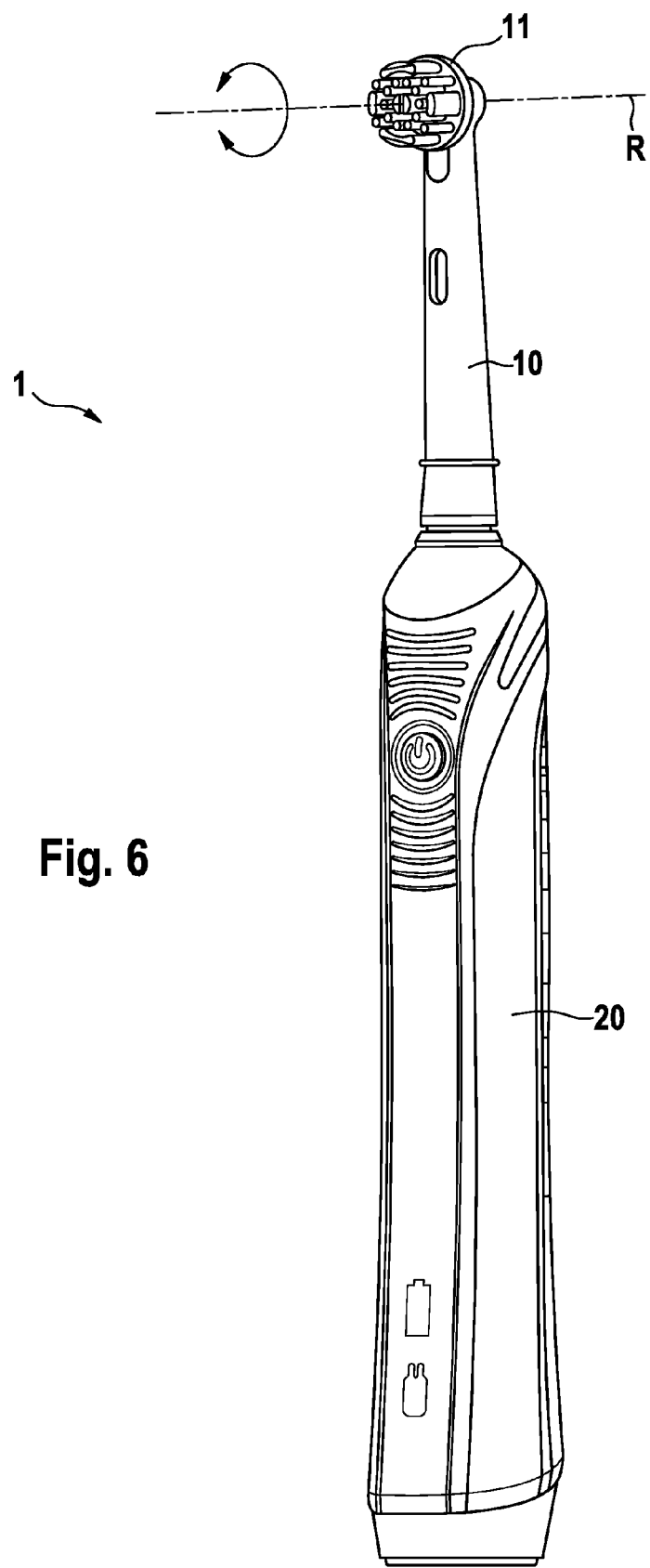
FIG. 6 is a depiction of an electric device that may comprise a resonant motor unit as proposed.

FIG. 1 shows an example embodiment of a resonant motor unit 800 comprising a resonant motor L and a control circuitry for controlling the resonant motor L. In the shown example embodiment, the resonant motor L is arranged in the bridge section of an H-bridge (also called a full bridge) arrangement having four switches S1, S2, S3, S4 (one switch being arranged in each of the legs of the H-bridge). The switches S1, S2, S3, S4, may be realized as MOSFETs in one embodiment, or as other switching devices such as transistors in other embodiments. Each of the switches S1, S2, S3, S4 may include a protective element such as a protective diode arranged parallel to the switch to protect the switch from over-voltages and to allow for commutation of current over the protective diode, e.g. when a current flow through the inductor of the resonant motor L (i.e. the coil of the resonant motor L) is switched off. In some embodiments, the resonant motor unit 800 comprises a functional element coupled to the motor armature for driven movement during operation. The resonant motor unit 800 may be used in an electric device such as an electric toothbrush as shown in FIG. 6 or in an electric shaver, a tool, a household appliance etc.

As has been stated above, the armature of the resonant motor L can be driven into a periodic movement by applying a periodic drive force. This periodic drive force is generated by a control unit 400 switching the switches S1, S2, S3, S4 on and off within a driving cycle such that a supply voltage from a supply voltage source 500 may be applied at the resonant motor L in positive half cycles and negative half cycles. During a positive half cycle of a driving cycle, the supply voltage may be applied in a positive direction, e.g. S1 and S4 are closed while S2 and S3 are open, and in a negative half cycle of the driving cycle, the voltage may be applied in a negative direction, e.g. S2 and S3 are closed while S1 and S4 are open. If the resonant motor L is not continuously driven (i.e. not continuously supplied with energy), damping typically inherently present in any real system would gradually reduce the motor amplitude until the moving motor armature stops.

At constant driving frequency $f_d$ and constant resonance frequency (for example in no load condition $f_R$, and in a loaded condition $f_r$) the amplitude of the moving motor armature can be varied by increasing or decreasing the driving force (i.e. by increasing or decreasing the energy that is periodically put into the resonant motor). The increasing or decreasing of the driving force can be accomplished by increasing or decreasing the time length of the driving phases (i.e. the time length during which the supply voltage is applied at the resonant motor L).

Further, the control unit 400 may control the switches S1, S2, S3, S4, to short-circuit the resonant motor L during at least a first short-circuiting phase following the driving phase. For example, the control unit 400 may close switches S1 and S2 or S3 and S4 during the short-circuiting phase (while the respective other two switches, S3 and S4 or S1 and S2, respectively, are open). The control unit 400 may further control the switches S1, S2, S3, S4, such that at least at a predetermined first time instant the first short-circuiting phase is concluded, and the current flow through the resonant motor (i.e. through the motor coil) is switched off, i.e. all switches are opened. Such phases of driving a resonant motor are generally described in DE 102 46 520 A1 together with potential further phases.

A voltage $U_M$ at the motor (measured against ground potential 600) may be provided at an input 700 of a measurement unit 401. The measurement unit 401 is in the shown embodiment realized as a part of the control unit 400. The measurement of the voltage $U_M$ may be performed in temporal synchrony with the switching-off of the current flow through the resonant motor L. The voltage signal provided by the resonant motor L when the current flow is switched off may then be evaluated by an evaluation unit 402 that in the shown embodiment is also realized as a part of the control unit 400. The voltage $U_M$ is discussed further hereafter.

Generally, either one or both of the measurement unit 401 and the evaluation unit 402 may be realized as being separate from the control unit 400. Alternatively, at least two units from the group consisting of the control unit 400, the measurement unit 401, and the evaluation unit 402 may be realized as an integral unit, such as a microprocessor on which the functionalities of the combined units are realized.

When the resonant motor L is in a constantly driven state, the motor armature oscillates with constant amplitude as long as the (mechanical) load on the motor does not change. When the supply voltage is applied at the resonant motor L during a driving phase, a current flow builds up through the resonant motor L. The current flow build up is, inter alia, dependent on the difference between the driving frequency $f_d$ and the resonance frequency (either no load resonance frequency $f_R$ or effective resonance frequency $f_r$), i.e. the current flow rise is inter alia dependent on the phase shift between periodic driving force and driven periodic movement. When the motor is then short-circuited during a first short-circuiting phase directly following the driving phase, i.e. when the supply voltage is not applied across the motor coil anymore, then current flow is driven by the voltage induced in the motor coil via the moving motor armature. At the end of the first short-circuiting phase, the remaining current flow may be switched-off by opening all switches of the H-bridge during a switching off phase. This will be explained in more detail further below.

The total voltage $U_M$ across a resonant motor is given by a self-induced voltage, $U_L = L \cdot dI(t)/dt$, where L is the inductance of the coil and $dI(t)/dt$ is the temporal change of the motor current (i.e.

the first derivative of the motor current I(t) with respect to the time t), a movement-induced voltage $U_{ind}$ generated in the motor coil by the movement of the permanent magnets relative to the coil, and a voltage developing at the ohmic resistance of the motor coil, $U_R = I \cdot R$, where I is the motor current and R is the resistance of the motor coil, so that $$U_M = U_L + U_{ind} + U_R = L \cdot dI(t)/dt + U_{ind} + I \cdot R$$

It has here been omitted to indicate that all voltages appearing in this equation are time dependent, i.e. $U_M = U_M(t)$ etc. The movement-induced voltage $U_{ind}$ typically is sinusoidal due to its dependency on the movement of the driven armature with respect to the stator, which typically is sinusoidal. As previously said, the driven periodic movement has a phase shift to the periodic drive force, which is dependent on the difference between the (effective) resonance frequency of the resonant motor and the driving frequency.

In the following, the resonance frequency of a resonant spring-mass system such as a resonant motor in a no-load condition is denoted by $f_R$, the effective resonance frequency that develops when the resonant motor is loaded, i.e. when one of the relevant parameters defining the resonance frequency is changed, is denoted by $f_r$.

A resonant motor may be utilized in an electric device (e.g., an electric oral hygiene device or a hair removal device etc.) to drive a functional element into motion, in particular into an oscillating motion. In an embodiment in which the electric device is an oral hygiene device, such as an electric toothbrush, the functional element may be a brush head comprising a plurality of cleaning elements extending from a surface of the brush head. When the brush head is pressed against a surface, e.g. a tooth surface, then at least one of the effective mass of the resonant motor and the effective spring constant of the resonant motor is influenced. This pressure dependent influence of at least one of the effective mass or effective spring constant leads to a variation of the effective resonance frequency $f_r$ due to the dependence of the resonance frequency on these parameters (i.e. the effective resonance frequency of the electric device changes over time during operation in case the load on the resonant motor is changed). In an embodiment, the driving frequency $f_d$ is kept constant, while the effective resonance frequency $f_r$ is varied, e.g. due to pressure applied on the driven functional element. When a mechanical load is applied at the resonant motor, also the peak amplitude of the driven periodic movement is varied. It is stated here that in some embodiments the effective resonance frequency $f_r$ under applied mechanical load may not be considerable different to the resonance frequency $f_R$ of the resonant motor in a no-load condition. Nevertheless, a mechanical load applied at the resonant motor (i.e. at the functional element driven by the resonant motor) also has an effect on the peak amplitude of the driven periodic movement. Hence, applying a mechanical load at the resonant motor varies the movement induced voltage $U_{ind}$ with respect to phase shift and height of the peak amplitude. Similarly, the movement induced voltage $U_{ind}$ is changed with respect to the periodic driving force when the driving frequency $f_d$ is changed as this has an effect onto the phase shift between periodic driving force and driven periodic movement.

Figure 2A:
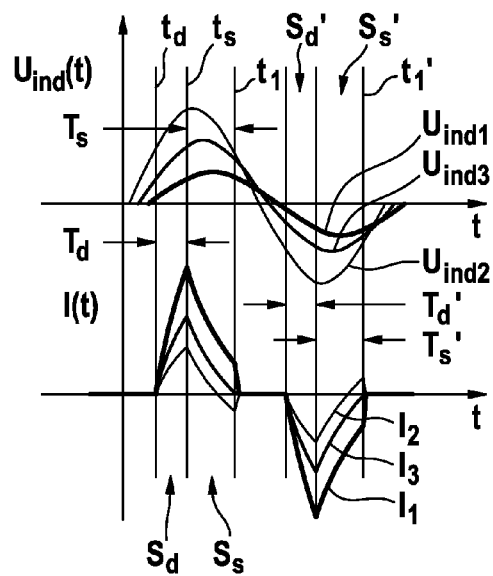
FIG. 2A is a schematic depiction of three movement-induced voltage curves relating to different applied loads and of respective curves of a current flow through the motor coil.

In the following, reference is made to FIGS. 2A and 2B. FIG. 2A shows the movement-induced voltage $U_{ind}(t)$ and the current flow I(t) through the motor coil for three different example cases. In the shown example cases, the load applied at the resonant motor is varied but the driving frequency is fixed. The shown curves relate to a single driving cycle during an equilibrium state of the resonant motor. The three example curves are indicated by Uind1, Uind2, and Uind3 for the movement-induced voltage and by I1, I2, and I3 for the current flowing through the motor coil. In these three exemplary curves, a time length $T_d$ of a first driving phase $S_d$ and a time length $T_s$ of a first short-circuiting phase $S_s$ following the driving phase $S_d$ and followed by a switching-off of the current flow at a fixed predetermined first time instant $t_1$ are fixed within the first (here: positive) half cycle.

The movement-induced voltage $U_{ind}(t)$ is phase shifted with respect to the position function (i.e.

the driven periodic movement) of the driven moving motor armature by −90 degrees. As at the centre position the velocity of the moving motor armature in the powered state is highest and thus the movement induced voltage is highest, the thick curve Uind1 shows a case where the (effective) resonance frequency is relatively far away from the driving frequency, and the thin line Uind2 shows a case where the resonance frequency is relatively close to the driving frequency. The medium line Uind3 indicates a case where the current flow is approximately zero at the predetermined first time instant $t_1$ at which the current flow is switched off.

It can further be seen that the peak amplitude of the movement-induced voltage is different for the three different curves Uind1, Uind2, and Uind3. In some embodiments, the change in the effective resonance frequency upon applied mechanical load may be relatively small, and the major change in the functional behavior of the movement-induced voltage is given by a change of the peak amplitude. In some other embodiments, the change of the effective resonance frequency and thus the change in the phase shift may be considered dominant. This behavior depends on the kind of motor used and on the kind of functional element driven by the resonant motor.

Figure 2B:
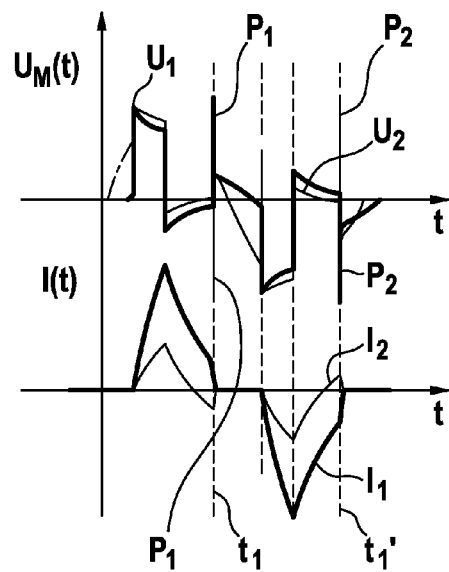
FIG. 2B is schematic depiction of the current flow and the total voltage across the resonant motor for the two most extreme cases of FIG. 2A.

FIG. 2B shows the (total) voltage $U_M(t)$ (of which $U_{ind}(t)$ is a component) across the resonant motor and again the current flow I(t) through the motor coil for the two extreme cases ($U_{ind1}$ and $U_{ind2}$) shown in FIG. 2A. The voltage across the motor $U_M(t)$ is indicated by U1 (thick line) and U2 (thin line), which curves correspond to the current flow indicated by lines I1 (thick line) and I2 (thin line), respectively.

Referring to FIGS. 2A and 2B, the resonant motor is driven at a constant driving frequency $f_d$. According to an embodiment of the control scheme of the present disclosure, in each driving cycle a first driving phase $S_d$ having a predetermined time length $T_d$ is provided, which first driving phase is followed by a first short-circuiting phase $S_s$ having a predetermined time length $T_s$. The driving phase $S_d$ and short-circuiting phase $S_s$ may be applied only in a first half-cycle (e.g. only in the positive or only in the negative half cycle) of a driving cycle. In the shown embodiment, the first half cycle is the positive half cycle.

In the shown embodiment, a second driving phase $S_d'$ and a second short-circuiting phase $S_s'$ may also be applied during the second half cycle (here: the negative half cycle) of the driving cycle. In another embodiment, no driving phase and no short-circuiting phase are applied during the second half cycle. In some embodiments, at least one of the second driving phase $S_d'$ and the second short-circuiting phase $S_s'$ applied in the second half cycle may have a different time length than their respective counterpart phase in the first half-cycle. In an embodiment, two or more driving phases may be applied in the first and/or second half cycle and each may be followed by a respective short-circuiting phase.

During the first driving phase $S_d$ (i.e., during the time period during which the supply voltage is applied at the resonant motor), a current flow I(t) builds up in the motor coil. The rise of the current flow is dependent, inter alia, on the phase shift ϕ between the periodic driving force and the driven periodic movement and further on the peak amplitude $U_{peak}$ of the movement-induced voltage $U_{ind}$. The peak amplitude $U_{peak}$ and the phase shift ϕ determine the actual height of the movement-induced voltage at a certain time instant t within the driving cycle, i.e. $U_{ind}(t)=U_{ind}(t; ϕ, U_{peak})$, and this actual height of the movement induced voltage influences the current flow build-up through the resonant motor. As these two factors are changed by a varying mechanical load applied at the resonant motor, the current flow build-up through the resonant motor depends on the applied load. Similarly, when the driving frequency $f_d$ is changed, at least the phase shift of the movement-induced voltage $U_{ind}$ with respect to the periodic driving force changes and thus the current-flow build-up during the driving phase will be influenced.

As said, these differences in the movement-induced voltage $U_{ind}$ influence, inter alia, the current build-up during the first (or second) driving phase $S_d$ (or $S_d'$). The current-flow build-up is also dependent on the driving phase start time $t_d$ at which the driving phase is initiated. In some embodiments, the driving phase start time $t_d$ may be chosen once and then kept fixed. Accordingly, when $t_d$ and $T_d$ are fixed, the current flow I(t) through the motor coil during the driving phase $S_d$ depends on the phase shift (i.e., on the difference between the driving frequency $f_d$ and the effective resonance frequency $f_r$) and on the peak amplitude of the motion-induced voltage $U_{ind}$, which are influenced by the mechanical load applied at the resonant motor or by varying the driving frequency.

A first short-circuiting phase $S_s$ having a predetermined time length $T_s$ can follow after the first driving phase $S_d$. The current flow through the motor coil is then driven by the movement induced voltage $U_{ind}$ and generally decreases during the first short-circuiting phase $S_s$. At the end of the first short-circuiting phase $S_s$, the current flow through the resonant motor may be switched off at a predetermined first time instant $t_1$. Depending on the various described factors, the height of the current $I(t_1)$ flowing through the coil of the resonant motor at the predetermined first time instant $t_1$ may be positive or negative (or may be just exactly zero) as is shown by the three example curves I1, I2, and I3. Thus, the current value $I(t_1)$ at the predetermined first time instant $t_1$ depends on the difference between driving frequency $f_d$ and effective resonance frequency $f_r$ (i.e. the phase shift) and on the peak amplitude of the motion-induced voltage.

When the current flow through the resonant motor changes its sign, also the total voltage at the resonant motor $U_M$ changes its sign. At the zero-crossing of $U_M$ (where the waveform $U_M$ crosses the time axis in FIG. 2B) at time $t_1$, the current flow is zero and the voltage lying at the ohmic resistance of the resonant motor $U_R$ is thus zero, $U_R=0$. Then, the self-induced voltage $U_L$ and the movement-induced voltage $U_{ind}$ are identical in voltage height but have different sign, i.e. $U_L=-U_{ind}$. While the total voltage at the motor is then zero, the two components adding up to zero need not necessarily be small. The absolute height of the movement-induced voltage relates to the residual energy in the resonant motor at switch-off. Typically, the current flow at the predetermined first time instant $t_1$ is not zero (but typically small); the voltage at the ohmic resistance is then also small as it is proportional to the current. The absolute height of the movement-induced voltage $U_{ind}$ then determines the residual energy in the motor at the switch-off instant.

When the current flow through the motor coil is switched off at the end of the first short-circuiting phase, the resonant motor responds with a first voltage signal $P_1$ allowing the residual current to commute over the protective diodes of the switches of the H-bridge circuit (so-called back electromagnetic force, B-EMF). The height of this voltage signal $P_1$ may be limited by a protective element, e.g. a protective diode being arranged parallel to each of the switches. Further, the height of the first voltage signal $P_1$ depends on the switching speed with which the relevant switch (e.g. S4 shown in FIG. 1, after a short-circuiting phase in which S3 and S4 were closed and S1 and S2 were open) is opened as the switching speed determines the change in current flow $dI(t)/dt$.

The sign of this first voltage signal $P_1$ depends on whether the residual energy in the resonant motor is positive or negative. In FIG. 2B the thick line I1 shows a case where the residual current flow at the predetermined first time instant $t_1$ is positive and the voltage at the resonant motor $U_M(t_1)$ is negative prior to the switch-off phase. In this case the sign of the first voltage signal $P_1$ is positive. The thin line I2 indicates a case where the residual current flow through the resonant motor is negative at the predetermined first time instant $t_1$ and the voltage at the resonant motor $U_M(t_1)$ as indicated by line U2 is positive prior to the switch-off phase. In this case the sign of the first voltage signal $P_1$ is negative.

In light of the above, in some embodiments, the system may be pre-calibrated so that the first voltage signal $P_1$ changes its sign under the condition that the applied load changes from being above (or below) a first predetermined load value to being below (or above) this value. In this manner, it may be determined whether the resonant motor has experienced a transition from an applied load less than a first predetermined load value D1 (shown in FIG. 3) to an applied load that is greater than the first predetermined load value D1 (e.g., a brush head of an electric toothbrush going from a non-engaged state to an engaged state wherein the brush head is applied to the surface of a user's tooth or teeth). As the time length $T_d$ of the driving phase $S_d$ may need to be fixed to periodically put a certain amount of energy into the resonant motor, the time length $T_s$ of the short-circuiting phase $S_s$ can be varied such that the sign change of the voltage signal occurs at the first predetermined time instant under a given applied load. Hence, this allows measuring when a certain load is applied onto the functional element driven by the resonant motor.

Similarly, the driving frequency $f_d$ may be changed between successive measurements and the predetermined first time instant $t_1$ may be chosen such that the sign change of the first voltage signal $P_1$ happens when the driving frequency $f_d$ coincides with the resonance frequency $f_R$ or when the driving frequency $f_d$ coincides with a target frequency $f_t$ that has a predetermined distance to the resonance frequency, $f_t=f_R+\Delta f$. In some embodiments, the control unit may be arranged to drive the resonant motor with a start driving frequency and may then successively change the driving frequency continuously, quasi-continuously or step-wise until a change in the sign of the voltage signal indicates that the current driving frequency has a predetermined distance to the resonance frequency. Hence, the control unit may be arranged to automatically determine the optimal driving frequency. By such a design, tolerances in the motor parts that lead to differences in the resonance frequency of a resonant motor when compared to other resonant motors of the same kind and/or aging of the motor parts that lead to differences of the resonance frequency of the resonant motor over time can be automatically coped with. In some embodiments, the control unit would employ a start driving frequency that should be above (or below) the resonance frequency that may occur due to tolerances and/or aging and the driving frequency would then successively be reduced (or increased) until the predetermined target frequency is reached.

In some embodiments, where only the sign change of the voltage signal $P_1$ is to be determined, it may be sufficient that the measurement unit only measures the sign of the voltage signal $P_1$. This can e.g. be realized by applying the first voltage signal $P_1$ at a standard digital input of a microcontroller where a voltage signal above a certain threshold signal is detected as a clear HIGH signal and any voltage signal below this threshold is detected as a LOW signal. In cases where the positive voltage signal could become so small that it may not be securely detected anymore as a clear HIGH signal (e.g. when the residual current flow is low and the movement-induced voltage is low at the predetermined first time instant), the switching speed of the respective switch or switches may be increased to generate a voltage signal that is (at least for a short period) high enough to be detectable as a clear HIGH signal. The measurement of the first voltage signal would then only need to deliver a binary single-digit output to the evaluation unit.

In some embodiments, the first voltage signal $P_1$ may be fed to a measurement unit realized as a high-speed analog circuitry that can detect the height of the first voltage signal as well as the width of the voltage signal. In some embodiments, a digital circuitry having temporal and voltage resolution being good enough to detect width and height of the voltage signal may be used. The evaluation unit may then have a storage unit having a predetermined table in which load values or frequency values may be assigned to height values and/or width values of the voltage signal such that the actual applied load value or the difference between the actual driving frequency to the resonance frequency can be computed from this table and the determined height and/or width values.

Figure 3:
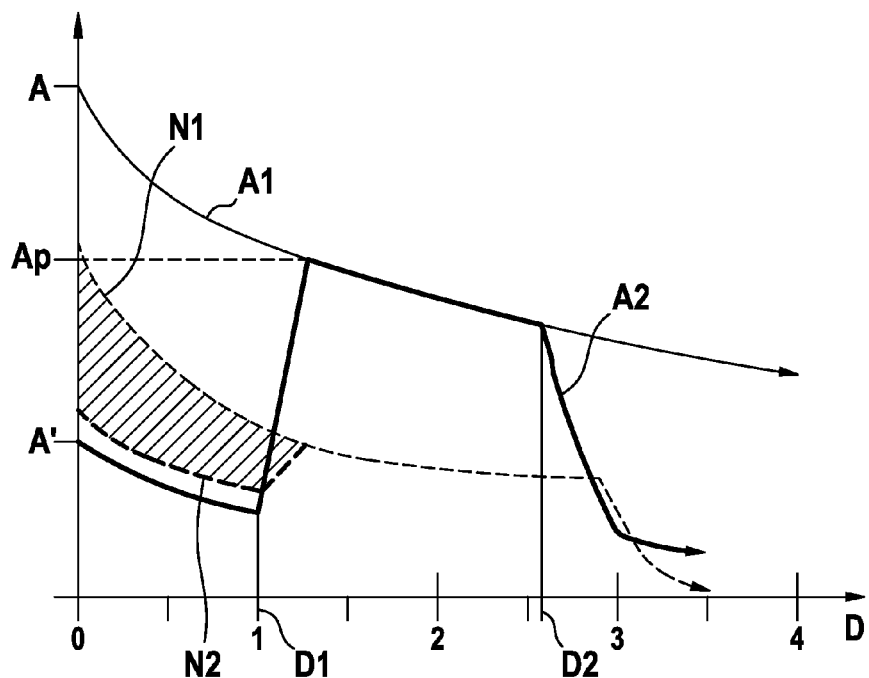
FIG. 3 is a schematic depiction of a control scheme of a resonant motor depending on a load level applied at the resonant motor.

When a sign change in the first voltage signal is detected, the control unit may then control the resonant motor in such a way that a driving parameter is changed. With reference to FIG. 2A and FIG. 3, the first driving phase $S_d$ may be increased by, for example, increasing the time length $T_d$ so that the moving motor armature moves with a desired higher peak amplitude $A_p$. Instead of increasing the time length $T_d$, an increase in the peak amplitude may also be achieved by increasing the applied supply voltage (e.g. by respective use of a step-up converter for boosting the voltage provided by the supply voltage source). In some embodiments, both the supply voltage and the time length $T_d$ may be increased in order to increase the amplitude.

The time length $T_d$ of the driving phase and the time length $T_s$ of the short-circuiting phase (together the total driving time length $T_{ds}$) may be chosen in accordance with the peak amplitude that is to be reached. For small peak amplitudes, the total driving time length $T_{ds}$ may be chosen to be about 1% of the length of the half cycle time length, while for high peak amplitudes, the total driving time length $T_{ds}$ may be chosen to be up to 99% of the half cycle time length. While the driving frequency $f_d$ may in general have every sensible value, the driving frequency $f_d$ may in some embodiments be in the range of between about 1 Hz to about 10,000 Hz. In an embodiment in which the electric device is realized as an oral hygiene device such as an electric toothbrush, the driving frequency $f_d$ may be in the range of between about 30 Hz to about 500 Hz. In some embodiments where the electric device is an electric toothbrush, the driving frequency $f_d$ may be greater than about 120 Hz. The driving frequency can be greater than about 120 Hz, greater than about 130 Hz, greater than about 140 Hz, greater than about 150 Hz, greater than about 160 Hz, greater than about 170 Hz, greater than about 180 Hz, greater than about 190 Hz, greater than about 200 Hz, or less than about 200 Hz, less than about 190 Hz, less than about 180 Hz, less than about 170 Hz, less than about 160 Hz, less than about 150 Hz, less than about 140 Hz, less than about 130 Hz, and/or any number or any range within or including these values.

Figure 4:
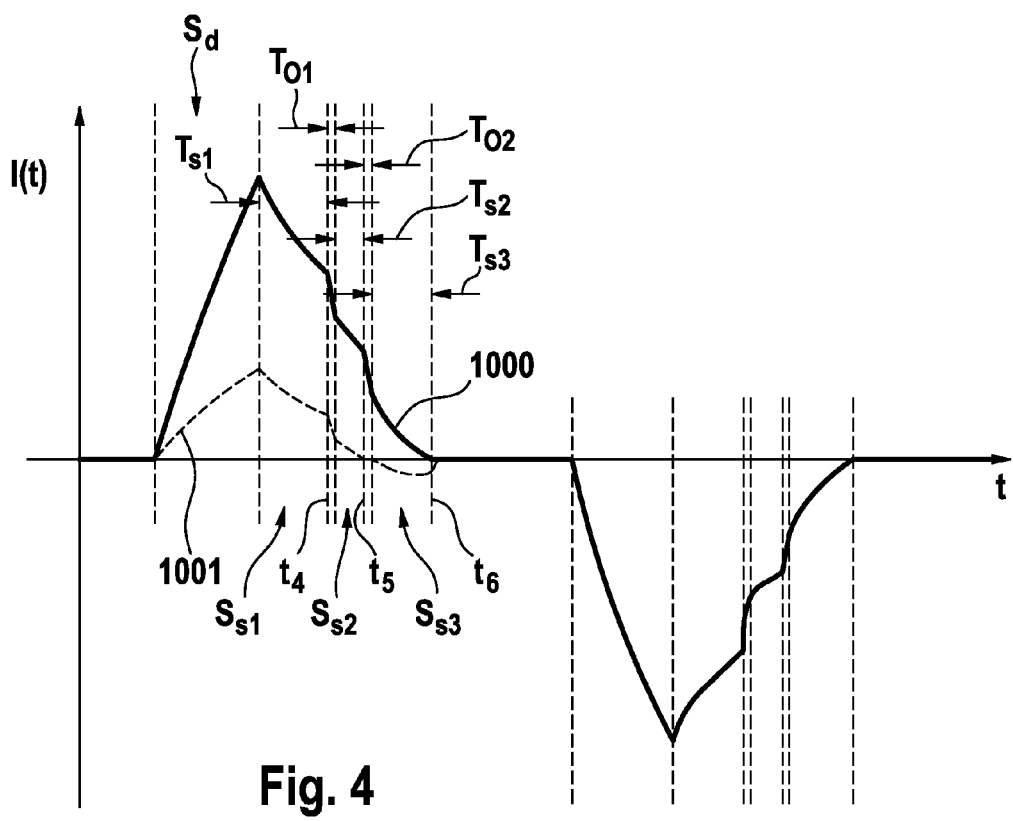
FIG. 4 is a schematic depiction of two examples of a current flow through a coil of a resonant motor where three predetermined measurement time instance are foreseen.

With reference to FIG. 4 it is noted that it is not required to first have a driving phase followed by a short-circuiting phase in order to generate a first voltage signal as described. In some embodiments, a first short-circuiting phase is initiated while no residual current flow through the motor coil is present (i.e. without a directly previous driving phase). For example, a first short-circuiting phase may follow after a relatively long switch-off phase that has allowed all residual current to commute over a protective diode (i.e. the short-circuiting phase starts without any residual current flow through the motor coil). Line 1001 in FIG. 4 shows a case where the residual current flow is zero after a switch-off phase initiated at time instant $t_5$. Current flow build-up through the motor coil is then driven by the movement-induced voltage during the first short-circuiting phase and hence is dependent on the sign of the motion-induced voltage. The current flow thus essentially changes its sign when the varying phase shift changes the sign of the movement-induced voltage (hence, embodiments where no considerable phase shift changes occur may not allow measuring any sign change). The relatively low current flow thus generated can then be used to generate the first voltage pulse by switching-off the current flow. In other words, this essentially simply probes the sign of the movement-induced voltage before the predetermined first time instant.

FIG. 3 is a schematic depiction showing peak amplitude curves A1 (thin line) and A2 (thick line) and corresponding noise level curves N1 (thin dashed line) and N2 (thick dashed line) for an electric device that shall work at a certain peak amplitude $A_p$ of the driven functional element of the electric device when a predetermined first load value D1 is achieved during operation. The predetermined first load value D1 relates to the pressure applied on the functional element which influences the phase shift of the movement-induced voltage with respect to the driving function (i.e. the effective resonance frequency is changed) and the peak amplitude of the movement-induced voltage. Without loss of generalization, it is assumed that the load applied at the functional element and the change of the phase shift (i.e. effective resonance frequency) and of the peak-amplitude of the movement-induced voltage have a clear functional relation for a given resonant motor unit.

Thin line A1 indicates the behavior of the peak amplitude of the oscillatory motion of a functional element driven by a resonant motor when mechanical load is applied on the resonant motor without applying the discussed control method. In contrast, thick line A2 indicates an example embodiment of the behavior of the peak amplitude of the functional element when a proposed control method is used. As indicated by the thick line A2, the control unit of the resonant motor unit may be arranged to drive the resonant motor at a predetermined driving frequency $f_d$ so that a low peak amplitude A' of the functional element is achieved when the electric device is switched on and/or under a load of less than D1. As depicted in FIG. 3, the start peak amplitude A of the functional element is higher than the start peak amplitude A' when the disclosed control method is employed.

Without loss of generality, the curves A1 and A2 here show a decrease in peak amplitude with increasing load D. With a resonant motor (or a control method for controlling a resonant motor) as proposed herein, the resonant motor may be driven at a desired peak amplitude $A_p$ when a first predetermined load value D1 is reached, and it may be driven at a low amplitude A' when the electric device is operated without load and/or at a load which is less than D1.

Low starting amplitude may provide a user with a perceivable signal of the operational state of the electric device. The low amplitude A' may also prevent water or any substance (e.g. toothpaste) that may be applied onto the functional element of the electric device from being splattered about. Additionally, a relatively low noise level may be achieved as is indicated by the thick dashed line N2 in comparison to the thin dashed line N1. N1 indicates the noise level of the electric device without the herein proposed resonant motor unit and/or control methods, respectively.

As will be explained in more detail further below, the resonant motor unit may also be arranged to measure and evaluate a second voltage signal that may be indicative of whether the applied load has changed from being above (or below) a second predetermined load value D2 to being below (or above) the second predetermined load value D2. This may allow for the control of the resonant motor with respect to this predetermined second load value D2. The control unit may in particular be arranged to drop to a low or even zero peak amplitude of the driven functional element when the second predetermined load value D2 is reached or exceeded as is schematically indicated by thick line A2. For example, when the resonant motor drives a functional element being a brush head of an electric toothbrush, it can be signaled to a user that teeth and gums are brushed with too high pressure by decreasing the amplitude and/or driving frequency. In addition or alternatively, the control unit may be arranged to indicate a certain applied load to a user. E.g. in the example as shown, a yellow light source may be lighted when the applied load is below the predetermined first load value D1 to indicate that the applied load is not effective for the intended purpose (e.g. tooth brushing). A green light source may be lighted when the applied load is between the predetermined first load value D1 and the predetermined second load value D2 to indicate that the applied load lies within a preferred range. A red light source may lighted if the applied load has reached or exceeded the predetermined second load value D2 to indicate to the user that a too high load is being applied. Any kind of indication can be utilized, e.g. instead of a visually perceivable indication, an audible indication may be used or a tangibly perceivable indication may be used.

Additionally, combinations of indications provided to the user are contemplated. For example, the control unit may decrease the amplitude and/or frequency, and an additional signal may be provided to the user. For example, the additional signal may include a visual, audible, tactile, the like or combinations thereof.

In an embodiment, at least two or more successive short-circuiting phases are each concluded by a switch-off phase as is schematically shown in FIG. 4, where the current flow I(t) through the motor coil is shown for two successive half cycles and where three predetermined time instances $t_4$, $t_5$, and $t_6$ were chosen to be able to discern three different predetermined load values. After a first driving phase $S_d$, the resonant motor is short-circuited during a first short-circuiting phase $S_{s1}$ having a time length $T_{s1}$ and then the current flow is switched off at a predetermined first time instant $t_4$ as was described above, but here the switch-off phase only lasts for a relatively short first switch-off time length $T_{O1}$. In case of a residual current flow through the motor coil being present at the switching-off instant, a first voltage signal will be provided by the resonant motor as was discussed above. The time length $T_{O1}$ of the first switch-off phase may be within a range of between about 5 microseconds and about 100 microseconds or of between about 20 microseconds to about 50 microseconds.

After the first switch off phase, the control unit short-circuits the resonant motor again during a second short-circuiting phase $S_{s2}$ having a time length $T_{s2}$. The time length $T_{s2}$ is chosen to be so small that the residual current flowing through the motor coil would only fully commute over the protective diode when the residual current flow is very small. Then the current flow is again switched off at a predetermined second time instant $t_5$. In case of a residual current flow through the motor coil being present at the switching-off instant, a second voltage signal will be provided by the resonant motor as was discussed above. The second switch-off phase may have a time length $T_{O2}$ that may also lie in a range of between about 5 microseconds and about 100 microseconds or of between about 20 microseconds to about 50 microseconds, as shown in FIG. 4.

Alternatively the second switch-off phase may continue until the start of a further driving phase. In the shown embodiment, a third short-circuiting phase $S_{s3}$ continues for a time length $T_{s3}$ after the second switch-off phase and is ended by a switch-off phase at a predetermined third time instant $t_6$. In case of a residual current flow through the motor coil being present at the switching-off instant, a third voltage signal will be provided by the resonant motor as was discussed above. In another embodiment, four or even more switch-off phases alternate with respective short-circuiting phases.

Line 1000 schematically indicates the current flow I(t) for an example embodiment where a current flow is present at the predetermined first time instant $t_4$ and at the predetermined second time instant $t_5$ and where the current flow just becomes zero at the predetermined third time instant $t_6$, i.e. the sign change of the third voltage signal that may be detected at the predetermined third time instant $t_6$ would then indicate that a load is applied at the resonant motor that has reached a predetermined third load value.

Line 1001 (only shown for the first half cycle) schematically indicates the current flow for an example case where a sign change of the second voltage signal measured at the predetermined second time instant $t_5$ may be detected indicating that a predetermined second load value is reached. As the current flow indicated by line 1001 is eliminated after the second switch-off phase, the third short-circuiting phase $S_{s3}$ here leads to a current flow build-up that is driven by the movement-induced voltage as was discussed above, and may produce a third voltage signal accordingly.

Figure 5:
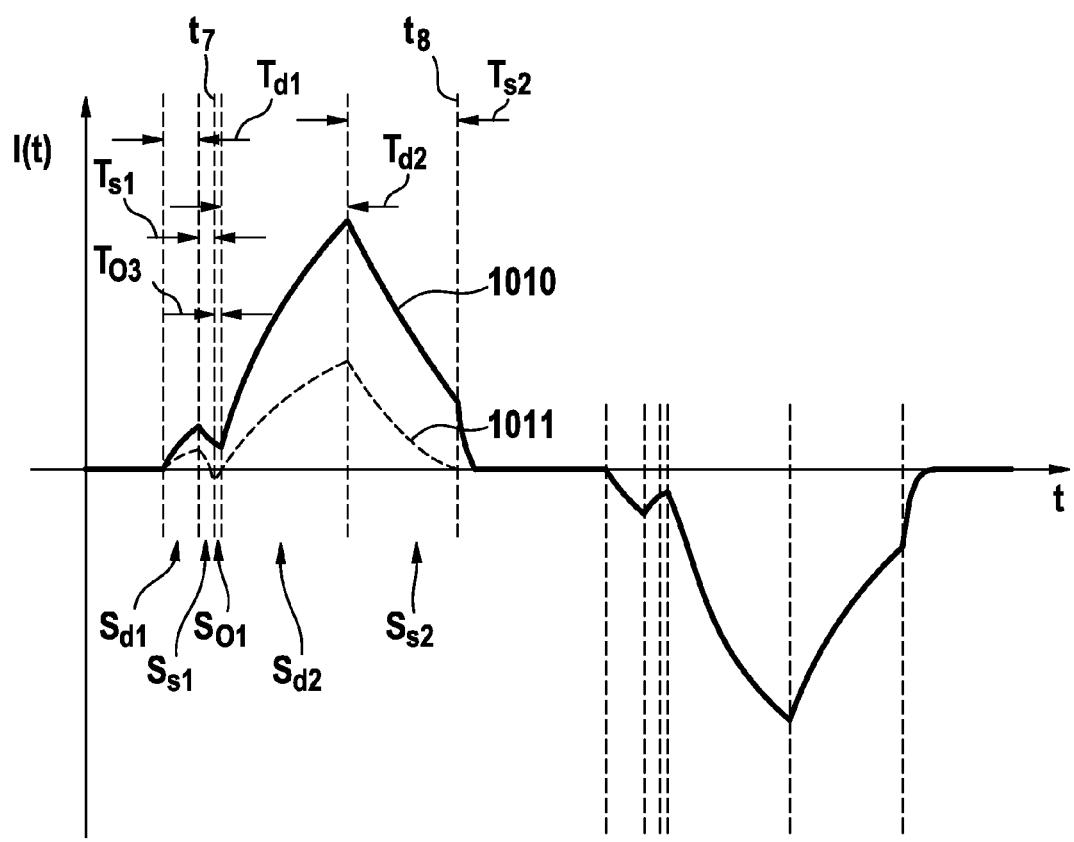
FIG. 5 is a schematic depiction of a current flow through the coil of a resonant motor where a predetermined measurement time instant is foreseen during a driving phase.

In another embodiment as shown in FIG. 5, a relatively short first driving phase $S_{d1}$ having a time length $T_{d1}$ is followed by a short first short-circuiting phase $S_{s1}$ having a time length $T_{s1}$ and which is ended at a predetermined first time instant $t_7$ by a relatively short switch-off phase $S_{O1}$ having a time length $T_{O3}$. The resulting first voltage signal developing after switching-off is then fed to the measurement unit. A second driving phase $S_{d2}$ that may have in some embodiments a longer time length $T_{d2}$ may start after the switch-off phase $S_{O1}$ and may be ended by a switch-off phase at a predetermined second time instant $t_8$ at which a developing second voltage signal may be measured.

The short switch-off phase $S_{O1}$ may have a time length $T_{O3}$ lying in the range of between about 5 microseconds to about 100 microseconds or of between about 20 microseconds to about 50 microseconds. The time length $T_{d1}$ of the first driving phase $S_{d1}$ and the time length $T_{s1}$ of the first short-circuiting phase $S_{s1}$ are set to time length values that allow the current flow to reduce to zero at the predetermined first time instant $t_7$ under a predetermined condition but that are also so short to allow a second driving phase $S_{d2}$ that may have a time length $T_{d2}$ that allows for achieving a high amplitude of the moving motor armature. The individual time lengths' may be empirically determined Generally, it is also possible to numerically simulate a resonant motor and its behavior and to determine the various parameters such as the predetermined time instants and time lengths' based on such a computer simulation.

Referring to FIG. 5, line 1010 indicates a case where the movement induced voltage is such that the current flow I(t) is relatively high and the residual current flow at the predetermined first time instant $t_7$ is positive. The resulting first voltage signal is then negative. Line 1011 indicates a case where the movement induced voltage has changed such that the current flow I(t) is lower than in the case indicated by line 1010 and the residual current flow at the predetermined first time instant $t_7$ is negative. The resulting first voltage signal is then positive.

Several possibilities exist to measure a second (or more generally: a further) voltage signal that is indicative of whether, e.g., an applied load has changed from being above (or below) a predetermined second (or further, i.e. third, fourth, . . . ) load value to being below (or above) this value. In an embodiment, the second predetermined load value may be chosen to be D2 as indicated in FIG. 3. In an embodiment, a different second driving phase $S_d'$ and/or a different second short-circuiting phase $S_s'$ may be applied in the second half cycle such that a second voltage signal $P_2$ that can be measured at a predetermined second time instant $t_1'$ (as shown in FIGS. 2A and 2B) indicates by its sign change a change of load applied at the resonant motor from being above (or below) a predetermined second load value to being below (or above) this value.

In an embodiment, two driving phases that are each followed by a respective short-circuiting phase are applied during at least a first half cycle (optionally in both half cycles), an example of which was shown and discussed with reference to FIG. 5, thus allowing to measure whether the applied load is below or above or between two predetermined load values (optionally more different predetermined load values can be probed).

In an embodiment, at least the length of one of the driving phase and the short-circuiting phase is periodically changed between successive driving cycles. For example, in a first driving cycle c1 a predetermined first load value is tested by the measurement, in the following second driving cycle c2 a predetermined second load value is tested, in the following driving cycle the predetermined first load value is again tested etc. This could be indicated by a c1-c2-c1-c2-c1-c2- . . . series. Other series could be contemplated such as c1-c2-c3-c1-c2-c3-c1-c2-c3- . . . or c1-c2-c1-c3-c1-c2-c1-c3- . . . or c1-c1-c2-c2-c1-c1-c2-c2- . . . etc.

Embodiments are contemplated which include the operation of memory elements. For example, where a user typically exceeds a second or third predetermined load value, the measurement sequences indicated above may be modified. Specifically, in the case of exceeding a third predetermined value, the series of measurement could be c1-c3, c-2-c-3, c1-c-3, c2-c3, . . . . This sequence could occur until the user changes their hygiene habits and begins to utilize appropriately applied force. At such time, the series of measurement may be modified to a previously listed series which measures during a cycle c3 less often.

In an embodiment, the time length of the first driving phase may be changed after the evaluation of the first voltage signal has indicated that the applied load has changed from being above (or below) a predetermined first load value to being below (or above) this value. The predetermined first time instance may then be changed too. In an embodiment, a predetermined second time instant is added after the above mentioned change of the time length of the first driving phase to allow measuring whether the applied load has changed back to above (or below) the predetermined first load value or has changed from being above (or below) a predetermined second load value to being below (or above) this value.

All the various possibilities to test whether more than one predetermined load value is reached can be combined with each other to the extent that this is possible.

As the peak amplitude at which the resonant motor is driven may be changed from low amplitude to high amplitude when the first voltage signal changes its sign, the load value D1 indicated in FIG. 3 should relate to a load applied at the functional element that indicates that the electric device is being used as it is, e.g., pressed against a surface. The respective predetermined first or second load value may be set to be within a range of between about 0.1 Newton (N) to about 5 N. The predetermined first load value may in particular be chosen to be within a range of between about 0.5 N to about 1.5 N for the first voltage signal and for the predetermined second load value between about 1.5 N to about 3.5 N for the second voltage signal. The electric device may additionally be equipped with an indicator to indicate to the user when the applied load is below the predetermined first load value level (e.g. by a yellow light element), when the applied load is between the predetermined first and second load values (e.g. with a green light element) or when the applied load is above the predetermined second load value (e.g. with a red light element).

In an above described example embodiment, a driving parameter that was changed after the evaluation unit had detected a change of the applied load from being above (or below) a predetermined first (or second, or third, . . . ) load value to being below (or above) this value was the time length of the first driving phase. Instead of changing the time length of the first driving phase, another driving parameter or several driving parameters could be changed, e.g. the driving frequency could be changed, the height of the supply voltage could be changed, the start time of the first driving phase within a half cycle could be changed etc.

FIG. 6 is a depiction of an electric device realized as an oral hygiene device 1, here in the form of an electric toothbrush. The oral hygiene device 1 comprises a handle 20 and an attachment 10. The attachment 10 comprises a functional element 11 mounted for driven oscillatory motion around a rotation axis R as indicated by a double arrow 12. The functional element 11, here realized as a brush head comprising a plurality of cleaning elements that are here realized as bristle tufts, may be driven by a resonant motor such that the functional head 11 oscillates about the rotation axis R. During operation, the resonant motor is controlled by a control unit.

As described in more detail below, in the context of an exemplary oral hygiene device, such as an electric toothbrush, the resonant motor may be controlled initially with relatively low operational amplitude to indicate to the user that the electronic toothbrush is in an on-state and is functional. When the brush head of the electric toothbrush is pressed against a surface in a user's oral cavity, the applied mechanical load of the resonant motor may change, and the resonant motor may be controlled to have higher operational amplitude (the working amplitude) when the applied load value reaches or exceeds a predetermined first load value. The low operational amplitude may be chosen to lie in a range of between about 1% to about 75% of the working amplitude or in a range of between about 5% to about 30%.

While various example embodiments were discussed, it is stated that all features that are disclosed in the present description, whether as isolated features or as a feature within the context of other features, are intended to be individually combinable with each other to the extent that this is possible and is not in contradiction with the gist and scope of the present disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A resonant motor unit comprising:
   a resonant motor;
   a control unit for driving the resonant motor at a driving frequency, for short-circuiting the resonant motor during a first short-circuiting phase in successive driving cycles and for concluding the at least first short-circuiting phases by switching off the current flow through the resonant motor at least at a predetermined first time instant within the driving cycles;

a measurement unit for successively measuring at least a first voltage signal provided by the resonant motor at the predetermined first time instant; and an evaluation unit for determining whether the first voltage signal has changed between successive measurements.

2. The resonant motor unit in accordance with claim 1, wherein the measuring unit is arranged to only measure the sign of the first voltage signal.

3. The resonant motor unit in accordance with claim 1, wherein the predetermined first time instant is predetermined such that the first voltage signal changes its sign when a load applied at the resonant motor changes from being below to above or from being above to below a predetermined first load value.

4. The resonant motor unit in accordance with claim 1, wherein
the control unit is further arranged for short-circuiting the resonant motor during a second short-circuiting phase in successive driving cycles and for concluding the second short-circuiting phases by switching off the current flow through the resonant motor at a predetermined second time instant within the driving cycles;
the measurement unit is further arranged for measuring a second voltage signal provided by the resonant motor at the predetermined second time instant; and
the evaluation unit is further arranged for determining whether the second voltage signal has changed between successive measurements.

5. The resonant motor unit in accordance with claim 4, wherein the measurement unit is arranged for either:
measuring the first voltage signal in a first half cycle of at least one of the successive driving cycles and the second voltage signal in a second half cycle of the same driving cycle; or
measuring the first voltage signal in a first half cycle of at least one of the successive driving cycles and the second voltage signal also in the first half cycle of the same driving cycle; or
measuring the first voltage signal within at least one of the successive driving cycles and the second voltage signal in at least one other of the successive driving cycles.

6. The resonant motor unit in accordance with claim 1, wherein the control unit is arranged to change the driving frequency between successive measurements.

7. The resonant motor unit in accordance with claim 6, wherein the predetermined first time instant is predetermined such that the first voltage signal changes its sign when the driving frequency coincides with the resonance frequency of the resonant motor or with a target frequency having a predetermined distance to the resonance frequency.

8. The resonant motor unit in accordance with claim 1, wherein the control unit is arranged to provide a supply voltage at the resonant motor during a driving phase prior to the short-circuiting phase.

9. The resonant motor unit in accordance with claim 1, wherein the control unit is arranged to change at least one parameter of the driving of the resonant motor when a change based on the first motor signal is determined and/or to indicate the determined change to a user.

10. An electric device comprising a resonant motor unit in accordance with claim 1, wherein the electric device is an oral hygiene device such as an electric toothbrush.

11. A method of controlling a resonant motor, the method comprising the steps of:
driving the resonant motor at a driving frequency;
short-circuiting the resonant motor during a first short-circuiting phase;
switching off a current flow through the resonant motor at least at a predetermined first time instant;
measuring at least a first voltage signal provided by the resonant motor at the predetermined first time instant; and
evaluating whether the first voltage signal has changed between successive measurements.

12. The method in accordance with claim 11 comprising the further step of changing at least a parameter of the driving of the resonant motor when a change based on the first voltage signal is determined and/or of indicating the determined change to a user.

13. The method in accordance with claim 11, further comprising the step of applying a supply voltage at the resonant motor prior to the act of short-circuiting of the resonant motor.

14. The method in accordance with claim 11 further comprising the steps of:
short-circuiting the resonant motor during a second short-circuiting phase;
switching off a current flow through the resonant motor at a predetermined second time instant;
measuring a second motor signal that is indicative of a load applied at the resonant motor; and
evaluating the measured second motor signal to determine whether the load value indicated by the second motor signal has changed from being above to below or from being below to above a predetermined second load value between successive measurements.

15. The method in accordance with claim 11 further comprising the step of changing the driving frequency between successive measurements.

* * * * *